(12) United States Patent
Platt et al.

(10) Patent No.: US 7,194,315 B1
(45) Date of Patent: Mar. 20, 2007

(54) COATED ELECTRODE AND METHOD OF MAKING A COATED ELECTRODE

(75) Inventors: Bruce Platt, Reistertown, MD (US); Allan S. Gelb, Orlando, FL (US)

(73) Assignee: Greatbatch-Hittman, Inc., Columbia, ND (US)

( * ) Notice: Subject to any disclaimer, the term of this patent is extended or adjusted under 35 U.S.C. 154(b) by 0 days.

(21) Appl. No.: 10/918,858

(22) Filed: Aug. 16, 2004

Related U.S. Application Data

(62) Division of application No. 09/730,314, filed on Dec. 5, 2000, now Pat. No. 6,799,076.

(60) Provisional application No. 60/169,370, filed on Dec. 7, 1999.

(51) Int. Cl.
*A61N 1/00* (2006.01)

(52) U.S. Cl. .................................................. 607/122

(58) Field of Classification Search ........ 607/119–132, 607/116
See application file for complete search history.

(56) References Cited

U.S. PATENT DOCUMENTS

| | | | |
|---|---|---|---|
| 4,167,607 A * | 9/1979 | de Nora et al. ............. 429/15 |
| 4,440,178 A | 4/1984 | Bussard et al. | |
| 4,542,752 A * | 9/1985 | DeHaan et al. ............. 607/119 |
| 4,584,079 A | 4/1986 | Lee et al. | |
| 4,602,637 A | 7/1986 | Elmqvist et al. | |
| 4,603,704 A | 8/1986 | Mund et al. | |
| 4,611,604 A | 9/1986 | Botvidsson et al. | |
| 4,679,572 A | 7/1987 | Baker, Jr. | |
| 4,784,160 A | 11/1988 | Szilagyi | |
| 4,919,135 A | 4/1990 | Phillips et al. | |
| 5,181,526 A | 1/1993 | Yamasaki | |
| 5,252,181 A | 10/1993 | Dutartre et al. | |
| 5,356,833 A | 10/1994 | Maniar et al. | |
| 5,427,631 A | 6/1995 | Johansson et al. | |
| 5,482,570 A * | 1/1996 | Saurer et al. ................ 136/255 |
| 5,587,200 A | 12/1996 | Lorenz et al. | |
| 5,609,611 A | 3/1997 | Bolz et al. | |
| 5,622,607 A | 4/1997 | Yamazaki et al. | |
| 5,645,580 A | 7/1997 | Moaddeb et al. | |
| 5,683,443 A | 11/1997 | Munshi et al. | |
| 5,853,411 A * | 12/1998 | Whayne et al. ................ 606/41 |
| 5,953,633 A | 9/1999 | Chen et al. | |
| 5,963,827 A | 10/1999 | Enomoto et al. | |
| 5,964,794 A | 10/1999 | Bolz et al. | |
| 6,006,133 A * | 12/1999 | Lessar et al. .................... 607/5 |
| 6,025,205 A | 2/2000 | Park et al. | |
| 6,071,476 A * | 6/2000 | Young et al. ................... 422/51 |
| 6,292,704 B1 * | 9/2001 | Malonek et al. ............. 607/121 |
| 6,430,447 B1 | 8/2002 | Chitre et al. | |
| 6,430,448 B1 | 8/2002 | Chitre et al. | |
| 2005/0075708 A1 * | 4/2005 | O'Brien et al. ............. 607/116 |

* cited by examiner

*Primary Examiner*—George Manuel
(74) *Attorney, Agent, or Firm*—Michael F. Scalise

(57) ABSTRACT

An electrode having a substrate with a first layer covering at least a portion of the substrate, and a second layer covering at least a portion of the first layer is disclosed. The first layer includes a porous layer consisting of a carbide, nitride or carbonitride of at least one of the metals titanium, vanadium, zirconium, niobium, molybdenum, hafnium, tantalum or tungsten. The second layer includes iridium.

In a method according to the present invention, a substrate is provided. A first layer is provided over at least a portion of the substrate, and a second layer is provided over at least a portion of the first layer. The first layer includes a layer consisting of a carbide, nitride or carbonitride of at least one of the metals titanium, vanadium, zirconium, niobium, molybdenum, hafnium, tantalum or tungsten. The second layer includes iridium.

27 Claims, 4 Drawing Sheets

COATED ELECTRODE AND METHOD OF MAKING A COATED ELECTRODE

CROSS REFERENCE TO RELATED APPLICATION

This application is a divisional of application Ser. No. 09/730,314, filed Dec. 5, 2000, now U.S. Pat. No. 6,799,076 to Gelb et al., which claims priority from U.S. Provisional Patent Application No. 60/169,370, filed Dec. 7, 1999.

BACKGROUND OF THE INVENTION

The present invention relates generally to coated electrodes and methods of making such electrodes.

SUMMARY OF THE INVENTION

The present invention includes an electrode having a substrate with a first layer covering at least a portion of the substrate, and a second layer covering at least a portion of the first layer. The first layer includes a porous layer consisting of a carbide, nitride or carbonitride of at least one of the metals titanium, vanadium, zirconium, niobium, molybdenum, hafnium, tantalum, or tungsten. The second layer includes iridium.

In a method according to the present invention, a substrate is provided. A first layer is provided over at least a portion of the substrate, and a second layer is provided over at least a portion of the first layer. The first layer includes a porous layer consisting of a carbide, nitride or carbonitride of at least one of the metals titanium, vanadium, zirconium, niobium, molybdenum, hafnium, tantalum or tungsten. The second layer includes iridium.

BRIEF DESCRIPTION OF THE DRAWINGS

For a fuller understanding of the nature and objects of the invention, reference should be made to the following detailed description taken in conjunction with the accompanying drawings, in which.

BEST MODE FOR CARRYING OUT THE INVENTION

Figure 1:
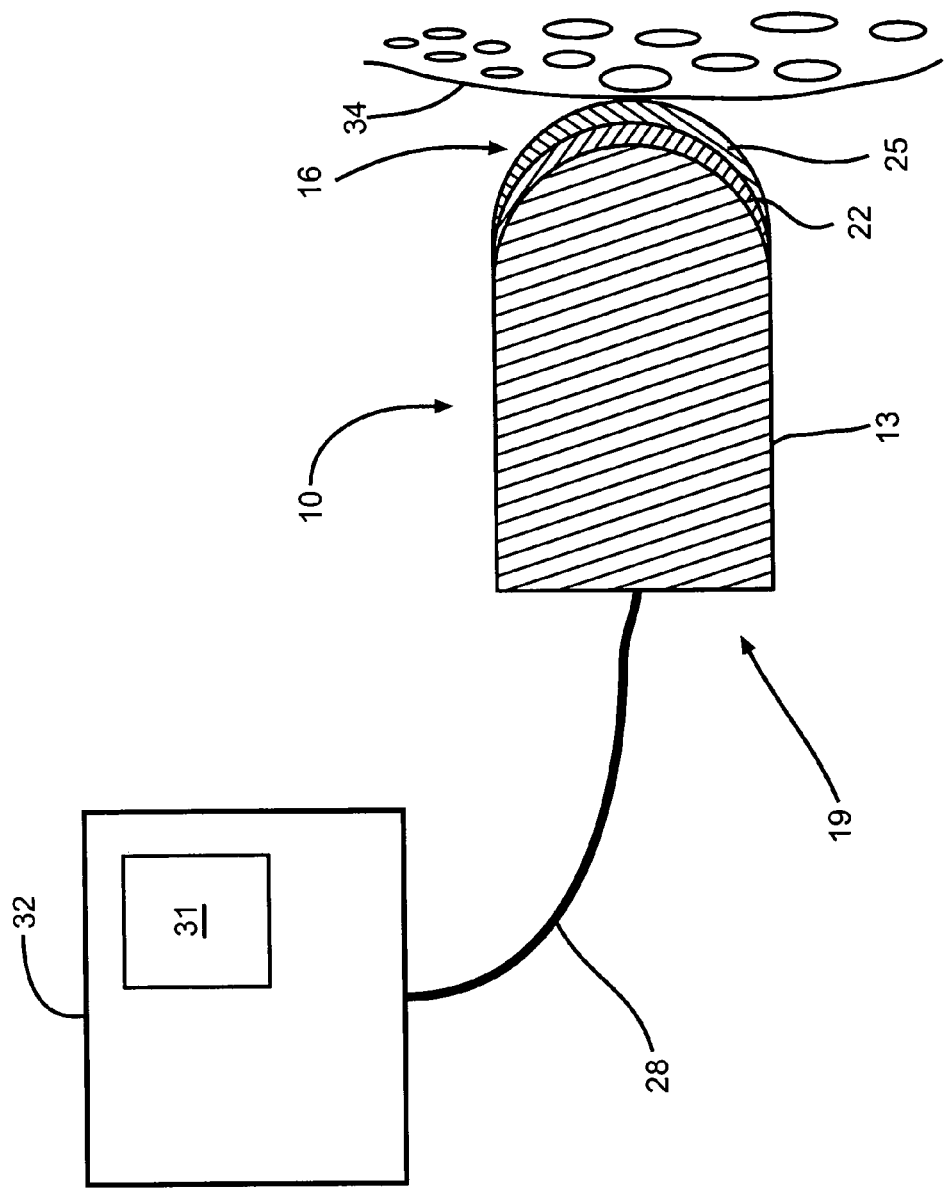
FIG. 1 is a cross sectional side view of an electrode according to the present invention.

FIG. 1 shows an electrode 10 according to the present invention. The electrode 10 has a substrate 13 with a first end 16 and a second end 19. The substrate 13 may include platinum, iridium, or both. For example, the substrate may be approximately 90% platinum and approximately 10% iridium. Other bio-compatible metals, such as titanium, may be suitable materials for the substrate.

The first end 16 has a first layer 22 and a second layer 25. The first layer 22 includes a porous layer of a carbide, nitride or carbonitride of at least one of the metals titanium, vanadium, zirconium, niobium, molybdenum, hafnium, tantalum or tungsten. The metals forming the carbides, nitrides and carbonitrides are all elements of the fourth through sixth sub-groups of the periodic system and thus include the transition metals. Carbides and nitrides of these transition metals include titanium carbide, titanium nitride, zirconium carbide, and tantalum nitride. The first layer may further include other layers such as a layer of titanium. The first layer 22 may contact a portion of the substrate 13.

The second layer 25 covers at least a portion of the first layer 22, and the second layer 25 may contact the first layer 22. The second layer 25 may be an outer surface of the electrode 10. The second layer 25 includes iridium, iridium oxide, or both.

In use, the second end 19 of the electrode 10 receives electricity to be delivered to the first end 16. The second end 19 may be electrically connected via an electrical conductor 28 to an energy source 31, such as an electrical pulse generator of a cardiac pacemaker 32. When connected to a cardiac pacemaker 32, the first end 16 senses signals from the heart and delivers the signals to the second end 19 where the signals are transmitted to the cardiac pacemaker 32 via the electrical conductor 28.

The present invention includes a cardiac pacing lead assembly. Such an assembly has an electrode, like that described above, wherein the second layer 25 is electrically connected to excitable cardiac tissue 34. The present invention also includes a cardiac pacemaker 32 having a pacing lead assembly connected to an electrical pulse generator, like those described above.

Figure 2:
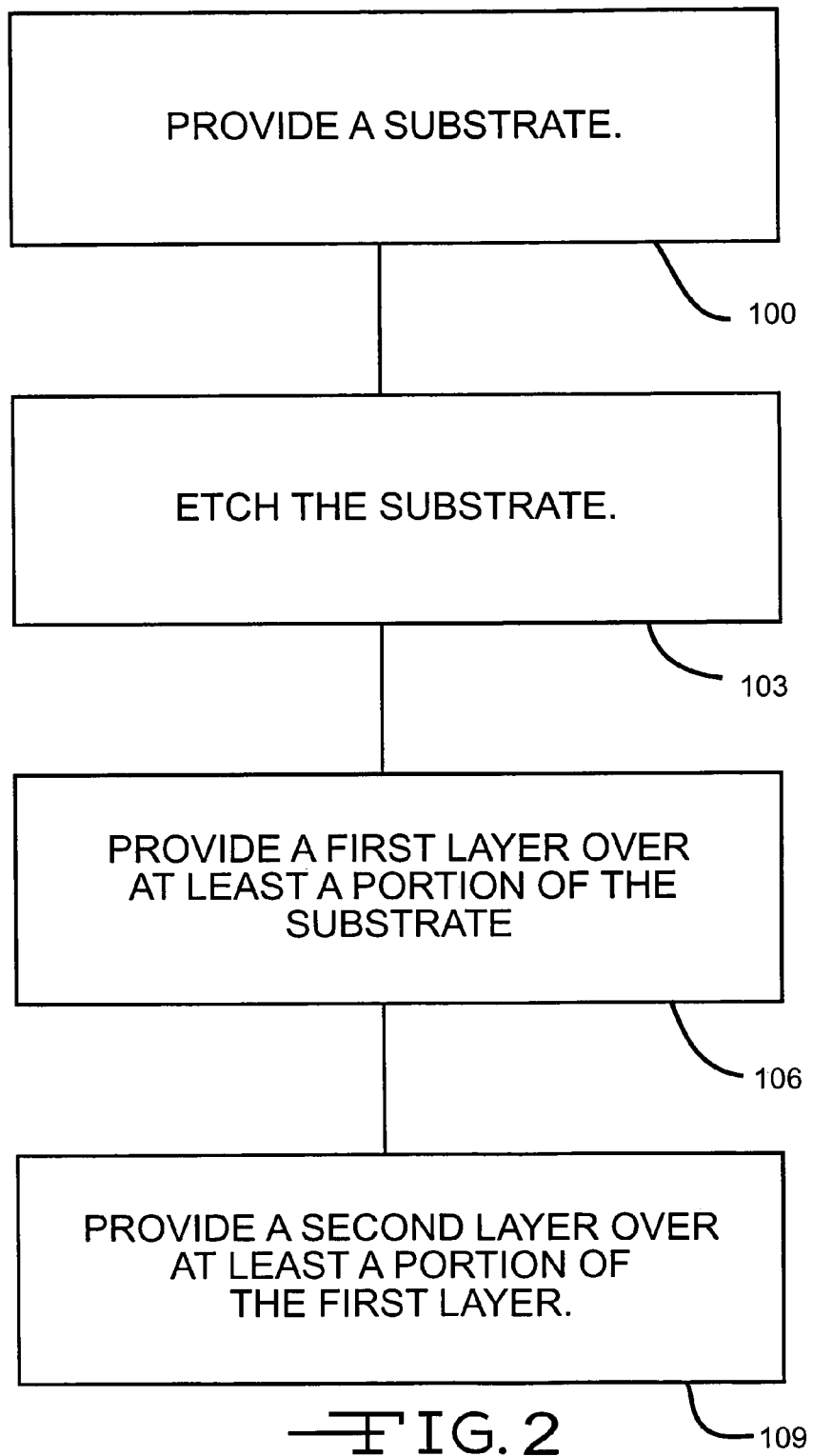
FIG. 2 illustrates a method according to the present invention.

FIG. 2 illustrates aspects of a method of making an electrode according to the present invention. In the method, a substrate, such as that described above, is provided 100. The substrate may be etched 103 to provide an etched substrate. Etching 103 the substrate may be performed in a sputter chamber by radio frequency ("RF") sputter etching. In one embodiment of the present invention, RF sputter etching occurs in an argon rich atmosphere.

A first layer is provided 106 over at least a portion of the substrate. To provide at least part of the first layer, an RF bias may be applied to the substrate while DC sputtering with titanium in the sputter chamber.

As noted above, the first layer includes a porous layer consisting of a carbide, nitride or carbonitride of at least one of the metals titanium, vanadium, zirconium, niobium, molybdenum, hafnium, tantalum or tungsten. For example, to provide a titanium nitride layer, DC sputtering with titanium may be carried out in a nitrogen rich atmosphere. In an embodiment of such a method, DC sputtering with titanium in a nitrogen rich atmosphere occurs for a period of time while an RF bias is applied to the electrode, for example via the substrate, and then for a period of time while no RF bias is applied to the electrode. Other embodiments of the present invention do not apply an RF bias to the electrode while sputtering with titanium in a nitrogen rich atmosphere.

A second layer is provided 109 on at least a portion of the first layer to provide the electrode. The second layer includes iridium, iridium oxide, or both, and may be provided using the sputter chamber.

An example of a method according to the present invention begins by providing a clean 90% platinum 10% iridium substrate. Sonicating the substrate with detergent, and rinsing with deionized water may clean the substrate. To aid in drying and cleaning, the rinsed substrate may be sonicated with acetone, and rinsed with 2-propanol.

Figure 3:
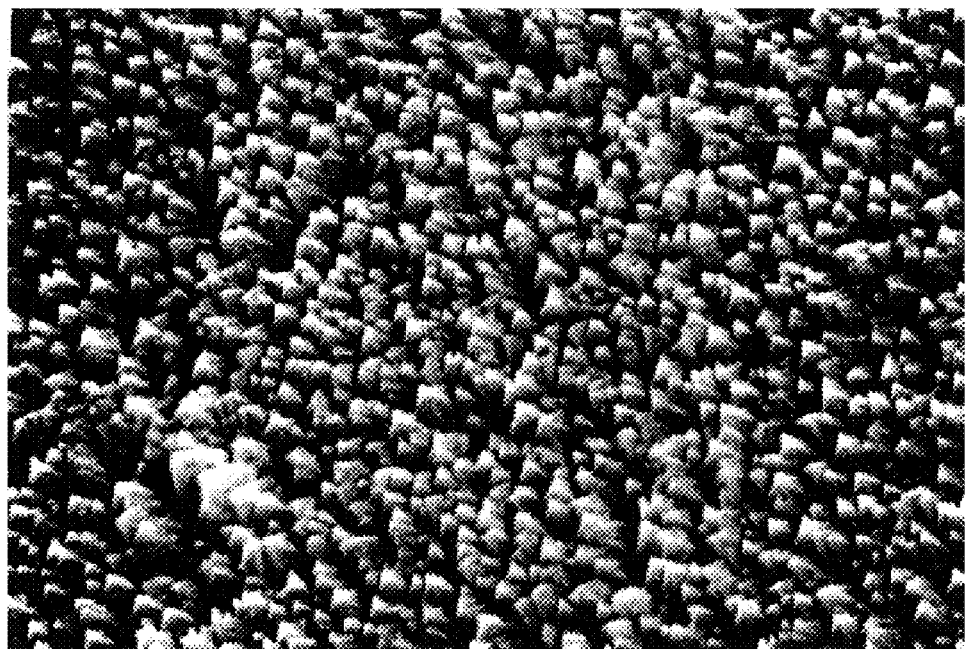
FIG. 3 shows an electron photo micrograph of a first layer according to the present invention.

The cleaned substrate is then placed in a sputter chamber, such as model number 8667 manufactured by Materials Research Corporation located in Orangeburg, N.Y. that has been modified to provide reactive sputtering capabilities. The chamber is evacuated to less than 5 micro torr. The substrate is then RF sputter etched at 500 watts in an atmosphere of 7.0 mtorr of argon for 18 minutes. The etched substrate is then direct current ("DC") sputtered with titanium for 2 minutes at 1 kW, with an RF bias applied to the substrate. Then nitrogen is introduced into the chamber at a combined pressure of 7 5 mtorr. After 18 minutes, the RF bias is removed, and the substrate continues to be sputtered with titanium for several hours at 1 kW. FIG. 3 shows a surface of a titanium-containing layer made according to the present invention.

Figure 4:
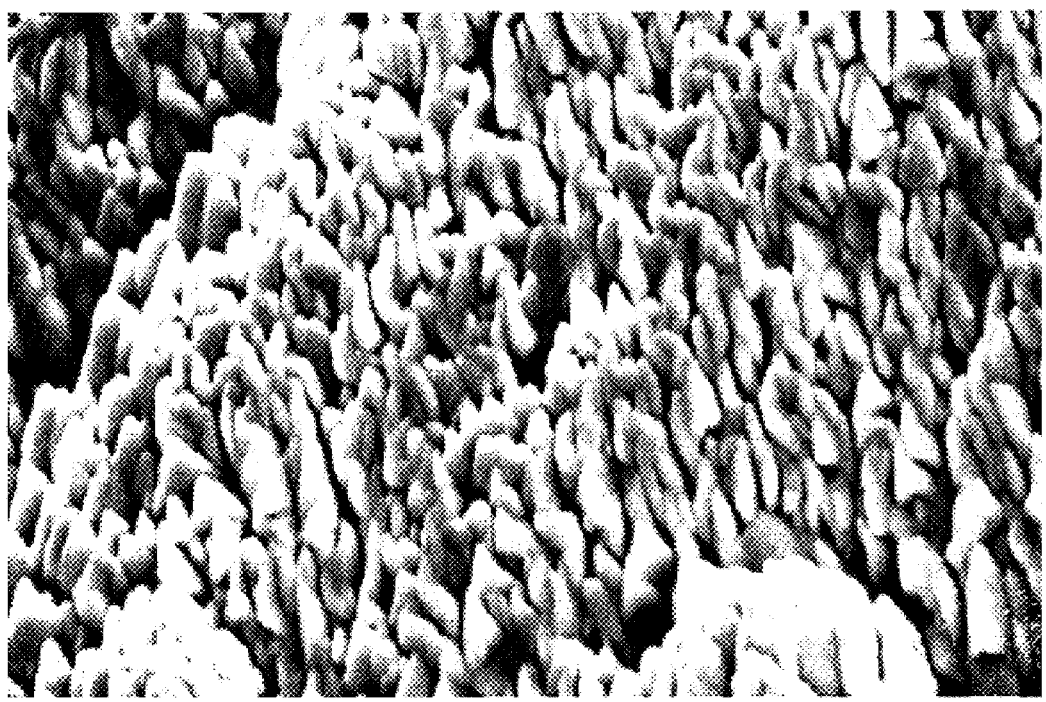
FIG. 4 shows an electron photo micrograph of a second layer according to the present invention.

The sputter chamber, with the titanium and titanium nitride coated substrate therein, is then evacuated to less than 5 micro torr. The titanium nitride coated substrate is sputtered with iridium for 30 minutes at 250 W RF. After performing this method, the iridium layer was found to be 0.27 microns thick. When exposed to air, at least some of the iridium may oxidize to form iridium oxide. FIG. 4 shows a surface of an iridium-containing layer made according to the present invention.

It is known that low values of polarization contribute to lower threshold voltages for the pacing function of a cardiac pacing electrode and of a defibrillation electrode. Low values of polarization also contribute to increased sensitivity for the sensing function of such electrodes. Low polarization may also contribute to greater efficacy in stimulation of other types of muscle tissue and in the detection of other electrical activity in the body. It is known that titanium nitride can be reactively sputtered to yield a morphology suitable for a low polarization coating on an electrode. Titanium nitride is widely used for electrode coatings, but there are concerns regarding the long-term stability of titanium nitride.

It is also known that iridium (which probably oxidizes to iridium oxide in air and more so after pulsing) or iridium oxide can lower the polarization of an electrode, although generally not to as low a value as titanium nitride. Furthermore, iridium and iridium oxide coatings on electrodes have been shown to prevent the growth of fibrotic tissue around such electrodes. However, neither iridium nor iridium oxide has the very desirable morphology of titanium nitride.

The present invention combines a layer of material selected from the group of a carbide, nitride or carbonitride of at least one of the metals titanium, vanadium, zirconium, niobium, molybdenum, hafnium, tantalum or tungsten, such as titanium nitride, with a layer of iridium, iridium oxide, or both. In doing so, the present invention achieves low polarization and prevents the growth of fibrotic tissue. Furthermore, the present invention promotes the long-term stability of the first layer by coating it with a second layer.

Although the present invention has been described with respect to one or more particular embodiments, it will be understood that other embodiments of the present invention may be made without departing from the scope of the present invention. Hence, the present invention is deemed limited only by the appended claims and the reasonable interpretation thereof.

What is claimed is:

1. An electrode, comprising:
   a) a substrate;
   b) a first layer having a porous morphology adapted for transmission of an electrical pulse to tissue and covering at least a portion of the substrate, wherein the first layer includes a material selected from the group consisting of a carbide, nitride, and carbonitride of the group consisting of titanium, vanadium, zirconium, niobium, molybdenum, hafnium, tantalum, tungsten, and mixtures thereof; and
   c) a second layer comprising iridium covering at least a portion of the first layer to thereby provide long term electrical stability to the material of the first layer.

2. The electrode of claim 1 wherein the second layer includes iridium oxide.

3. The electrode of claim 1 wherein the second layer is an outer surface of the electrode.

4. The electrode of claim 1 wherein the second layer covering the first layer are disposed at a first end of the substrate with an electrical conductor being electrically connected to a second end of the electrode.

5. The electrode of claim 1 wherein the substrate includes platinum.

6. The electrode of claim 1 wherein the substrate includes iridium.

7. The electrode of claim 1 wherein the first layer contacts the substrate.

8. The electrode of claim 1 wherein the second layer contacts the first layer.

9. A cardiac pacing lead assembly, comprising:
   a) an electrode comprising a substrate having a first end and a second end, and comprising a first layer of a material having a porous morphology adapted for transmission of an electrical pulse to fibrotic tissue and covering at least a portion of the first end of the substrate, and a second layer comprising iridium covering at least a portion of the first layer to thereby provide long term electrical stability to the first layer, wherein the material of the first layer is selected from the group consisting of a carbide, nitride, and carbonitride of the group consisting of titanium, vanadium, zirconium, niobium, molybdenum, hafnium, tantalum, tungsten, and mixtures thereof; and
   b) an electrical conductor electrically connected to the second end.

10. The lead assembly of claim 9 wherein the second layer includes iridium oxide.

11. The lead assembly of claim 9 wherein the second layer is an outer surface of the electrode.

12. The lead assembly of claim 9 further comprising an electrical conductor electrically connected to the second end of the electrode.

13. The lead assembly of claim 9 wherein the substrate includes platinum.

14. The lead assembly of claim 9 wherein the substrate includes iridium.

15. The lead assembly of claim 9 wherein the first layer contacts the substrate.

16. The lead assembly of claim 9 wherein the second layer contacts the first layer.

17. A cardiac pacemaker, comprising:
   a) an electrical pulse generator; and
   b) an electrode electrically connected to the pulse generator, the electrode comprising a substrate having a first end and a second end, and comprising a first layer of a material having a porous morphology adapted for transmission of an electrical pulse to tissue and covering at least a portion of the first end, and a second layer comprising iridium covering at least a portion of the first layer to thereby provide long term electrical stability to the first layer, wherein the material of the first layer-is selected from the group consisting of a carbide, nitride, and carbonitride of the group consisting of titanium, vanadium, zirconium, niobium, molybdenum, hafnium, tantalum, tungsten, and mixtures thereto.

18. The cardiac pacemaker of claim 17 wherein the second layer includes iridium oxide.

19. The cardiac pacemaker of claim 17 wherein the second layer is an outer surface of the electrode.

20. The cardiac pacemaker of claim 17 further comprising an electrical conductor electrically connected to the second end of the electrode and the pulse generator.

21. The cardiac pacemaker of claim 17 wherein the substrate includes platinum.

22. The cardiac pacemaker of claim 17 wherein the substrate includes iridium.

23. The cardiac pacemaker of claim 17 wherein the first layer contacts the substrate.

24. The cardiac pacemaker of claim 17 wherein the second layer contacts the first layer.

25. An electrode, comprising:
   a) a substrate comprising 90% platinum/10% iridium;
   b) a first layer comprising titanium nitride having a porous morphology adapted for transmission of an electrical pulse to tissue and covering at least a portion of the substrate; and
   c) a second layer comprising iridium oxide covering at least a portion of the first layer to thereby provide long term electrical stability to the titanium nitride.

26. An electrode, comprising:
   a) a substrate comprising a conductive material selected from the group consisting of platinum, iridium, tantalum, and mixtures thereof;
   b) a first layer comprising titanium nitride having a porous morphology adapted for transmission of an electrical pulse to tissue and covering at least a portion of the substrate; and
   c) a second layer comprising iridium oxide covering at least a portion of the first layer to thereby provide long term electrical stability to the titanium nitride.

27. An electrode, comprising:
   a) a substrate comprising a conductive material selected from the group consisting of platinum, iridium, tantalum, and mixtures thereof;
   b) a first layer having a porous morphology adapted for transmission of an electrical pulse to tissue and covering at least a portion of the substrate, wherein the first layer includes a material selected from the group consisting of titanium carbide, titanium nitride, zirconium carbide, tantalum nitride, and mixtures thereof; and
   c) a second layer comprising iridium oxide covering at least a portion of the first layer to thereby provide long term electrical stability to the material of the first layer.

* * * * *